US00PP23160P3

(12) United States Plant Patent
Slaughter et al.

(10) Patent No.: US PP23,160 P3
(45) Date of Patent: Nov. 6, 2012

(54) PEACH TREE, 'BURPEACHTWENTYSEVEN'

(50) Latin Name: *Prunus persica*
Varietal Denomination: Burpeachtwentyseven

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 73 days.

(21) Appl. No.: 12/928,917

(22) Filed: Dec. 20, 2010

(65) Prior Publication Data

US 2012/0159679 P1 Jun. 21, 2012

(51) Int. Cl.
*A01H 5/00* (2006.01)

(52) U.S. Cl. ..... Plt./197

(58) Field of Classification Search ..... Plt./197
See application file for complete search history.

*Primary Examiner* — June Hwu

(74) *Attorney, Agent, or Firm* — Paine Hamblen, LLP

(57) ABSTRACT

A new and distinct variety of peach tree (*Prunus persica*), which is denominated varietally as 'Burpeachtwentyseven', and which produces an attractively colored yellow-fleshed, freestone peach which is mature for harvesting and shipment approximately June 12 to June 19 under the ecological conditions prevailing in the San Joaquin Valley of central California.

1 Drawing Sheet

BACKGROUND OF THE NEW VARIETY

The present invention relates to a new, novel, and distinct variety of peach tree, '*Prunus persica*', and which has been denominated varietally as 'Burpeachtwentyseven'.

The present variety of peach tree resulted from an on-going program of fruit and nut tree breeding. The purpose of this program is to improve the commercial quality of deciduous fruit and nut varieties, and rootstocks, by creating and releasing promising selections of *Prunus, Malus* and *Juglans regia* species. To this end we make both controlled and hybrid cross pollinations each year in order to produce seedling populations from which improved progenies are evaluated and selected.

The seedling, 'Burpeachtwentyseven' was originated by us, and selected from a population of seedlings growing in our experimental orchards which is located near Fowler, Calif. The seedlings, grown on their own roots, were derived from a cross that was made in 1996 of the acidic, yellow-fleshed, peach which is identified as 'Spring Gem' and which is the pollen parent, (unpatented) and the nectarine variety identified as B17.013, and which is an early mid-season, white fleshed, non-melting, clingstone nectarine, and which is the seed parent. As the fruit ripened the resulting seed from this cross, was stratified, germinated and then was subsequently grown in a greenhouse to an appropriate development stage. Subsequently, the new plants were field planted and grown for further evaluation. One seedling, which is the present variety, exhibited especially desirable characteristics, and was then designated as 'E8.017'. This seedling was marked for subsequent observation. After the 1999 fruiting season, the new variety of peach tree 'E8.017', now named 'Burpeachtwentyseven' was selected for advanced evaluation and repropagation.

ASEXUAL REPRODUCTION

Asexual reproduction of this new and distinct variety of peach tree was accomplished by budding the new peach tree 'E8.017' onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachtwentyseven' is a new and distinct variety of peach tree, which is considered of medium to medium large size, and which has a moderately vigorous growth characteristic. This new peach tree is also a regular and productive bearer of relatively large, firm, yellow-fleshed, clingstone fruit which have a good flavor and eating qualities. This new peach tree has a medium chilling requirement of approximately 650 hours, and further produces relatively uniformly sized fruit throughout the tree. In addition to the foregoing, the fruit of the new peach tree also appears to have good handling and shipping qualities.

The 'Burpeachtwentyseven' peach tree bears fruit which are ripe for commercial harvesting and shipment on approximately June 12 to June 19 under the ecological conditions prevailing in the San Joaquin Valley of central California. In relative comparison to the 'Burpeachsix' peach tree (U.S. Pat. No. 13,392), which produces fruit having a similar harvesting date, the new variety of peach tree bears fruit which is firmer and has a higher degree of red blush color on the skin surface. Further the new peach variety exhibits a clingstone character which is in contrast to the fruit of the 'Burpeachsix' peach tree which is freestone. These distinctions are displayed when both varieties have been grown and evaluated under the same cultural conditions, and at the same geographical location. Further, the fruit of the subject variety generally exhibits a larger fruit diameter (approximately 5-8 mm larger) than the pollen parent peach 'Spring Gem' (unpatented), and the current variety ripens approximately 15-18 days later than the seed parent peach tree B17.013.

BRIEF DESCRIPTION OF THE DRAWINGS

The accompanying drawing, which is provided, is a color photograph of the new peach tree variety. The photograph depicts two whole mature fruit showing the top and bottom characteristics thereof, and one mature fruit bisected laterally along the equatorial plane, and which reveals the flesh characteristics thereof. The external coloration of the fruit as shown in the photograph is sufficiently matured for harvesting and shipment. Additionally the photograph displays a sample vegetative shoot bearing typical leaves, and a typical stone with the flesh removed, and which displays the surface characteristics thereof.

The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display the botanical, pomological or other characteristics as set forth, hereinafter. Therefore, this disclosure may not be relied upon to support any future legal claims, including, but not limited to, breach of warranty of merchantability, or fitness for any particular purpose, or non-infringement which is directed, in whole, or part, to the present variety.

DETAILED DESCRIPTION

Referring more specifically to the pomological details of this new and distinct variety of peach tree, the following has been observed during the seventh fruiting season under the ecological conditions prevailing at the orchards of the assignee which are located near the town of Fowler, county of Fresno, state of Calif. All major color code designations are by reference to The R.H.S. Colour Chart (Fourth Edition) provided by The Royal Horticultural Society of Great Britain. Common color names are also occasionally used.

TREE

Size: Generally. Considered medium to medium large as compared to other common commercial peach cultivars ripening in the early season of maturity. The tree of the present variety was pruned to a height of approximately 270.0 cm to about 310.0 cm at commercial maturity.

Vigor: Considered vigorous. The present peach tree variety grew from about 172.0 cm to about 180.0 cm in height during the first growing season. The new variety was pruned to a height of approximately 150.0 cm during the first dormant season, and primary scaffolds were then selected for the desired tree structure.

Productivity: Productive. Fruit set varies from more than the desired crop load to levels much higher than desired levels when grown in a suitable horticultural zone, and under appropriate commercial conditions. The fruit set is spaced by thinning to develop the remaining fruit into the desired market-sized fruit. The number of the fruit set varies with the prevailing climatic conditions and the cultural practices employed. Therefore productivity is not a distinctive characteristic of the new variety.

Fruit bearing: Regular. Fruit set has been more than adequate during the previous years of observation, and thinning was necessary during the past 8 years on both the original seedling and on subsequent asexually reproduced trees.

Form: Upright, and pruned into a vase shape.

Density: Considered moderately dense. It has been discovered that pruning the branches from the center of the tree to obtain a resulting vase shape allows for air movement and appropriate amounts of sunlight to enhance fruit color, and renewal of fruiting wood throughout the tree.

Hardiness: The present tree was grown and evaluated in USDA Hardiness Zone 9. The calculated winter chilling requirements of the new tree is approximately 650 hours at a temperature below 7.0 degrees C. The present variety appears to be hardy under typical central San Joaquin Valley climatic conditions.

TRUNK

Diameter: Approximately 17.5 cm in diameter when measured at a distance of approximately 15.24 cm above the soil level. This measurement was taken at the end of the seventh growing season.

Bark texture: Considered moderately rough, with numerous folds of papery scarfskin being present. Since bark development and coloration change with advancing tree age this characteristic varies with the tree vigor, age and regional conditions. Therefore, this is not a dependable descriptor of the new variety.

Lenticels: Numerous flat, oval lenticels are present. The lenticels range in size from approximately 4.0 millimeters to about 6.0 mm in width, and between about 1.0 and about 2.0 millimeters in height. The development and size of the trunk lenticels can be influenced, to some degree, by the ambient growing conditions and are not, necessarily, a dependable characteristic of this variety. As trees of this variety mature, lenticels are present, but they are generally covered by increasing layers of cork (mature bark) and therefore become less apparent.

Lenticel color: Considered an orange brown, (RHS Greyed-Yellow Group 162 B).

Bark coloration: Variable, but it is generally considered to be a medium brown, (RHS Greyed-Orange Group 166 D). This bark description was taken from trees in their seventh leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

Size: Considered medium for the variety.

Diameter: Average as compared to other peach varieties. The branches have a diameter of about 9.0 centimeters when measured during the seventh year after grafting.

Surface texture: Average, and appearing furrowed on wood which is several years old.

Crotch angles: Primary branches are considered variable, and are usually growing at an angle of about 50 to about 60 degrees when measured from a horizontal plane. This characteristic can be influenced, to some degree, by tree vigor, rootstock and other cultural conditions.

Current season shoots:

*Surface texture.*—Substantially glabrous.

Internode length: Approximately 2.5 cm.

Color of mature branches: Grey brown, (RHS Grey-Orange Group 174 A).

Current seasons shoots:

*Color.*—Medium-light green, (RHS Green Group 144 A). The color of new shoot tips is considered a bright and shiny green (RHS Green Group 141 A). The vegetative shoot color can be significantly influenced by plant nutrition, irrigation practices, and exposure to sunlight, and therefore should not be considered a consistent botanical characteristic of this new variety.

LEAVES

Size: Considered medium for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and cultural factors listed above, and are not typically considered a dependable botanical descriptor. Leaf bud burst occurs approximately 1 to 2 weeks after the first bloom under typical cultural conditions.

Leaf length: Approximately 145.0 to about 167.0 millimeters.

Leaf width: Approximately 29.0 to about 33.0 millimeters.

Leaf base-shape: The leaves generally exhibit equal marginal symmetry relative to the leaf longitudinal axis.

Leaf form: Lanceolate.

Leaf tip form: Acuminate.

Leaf color:

*Upper leaf surface.*—Dark green, (approximately RHS Green Group 131 B).

Leaf texture: Glabrous.

Leaf color:

*Lower surface.*—Deep green, (approximately RHS Yellow-Green Group 146 B).

Leaf venation: Broadly pinnately veined.

Mid-vein:

*Color.*—Considered a light yellow-green, (approximately RHS Yellow-Green Group 150 C) in the early to mid-period of the growing season.

Leaf margins: Gently undulating.

*Form.*—Considered bluntly serrate, occasionally biserrate.

*Uniformity.*—Considered generally uniform.

Leaf petioles:

*Form.*—Considered canaliculated, that is, having a shallow channel and more pronounced trough from the dorsal aspect. The petiole margin is considered rounded when viewed from the ventral aspect.

*Size.*—Considered medium large for the species.

*Length.*—About 9.0 to about 12.0 mm.

*Diameter.*—About 1.5 to about 2.5 mm.

*Color.*—Pale green, (approximately RHS Yellow-Green Group 146 C).

Leaf glands:

*Size.*—Considered small for the species; approximately 1.0 mm in length; and about 1.0 mm in height.

*Number.*—Generally one to two glands per marginal side are found. Observations of more than two glands per marginal side are more uncommon.

*Type.*—Generally considered to be a tight, small reniform shaped gland.

*Color.*—Considered a pale green, approximately (RHS Green Group 143 B). Typically the coloration of the glands darkens, and occasionally begins to desiccate during, and after, the mid-late growing season.

Leaf stipules:

*Size.*—Medium large for this variety.

*Number.*—Typically 2 per leaf bud, and up to 6 per shoot tip.

*Form.*—Lanceolate in form, and having a serrated marginal edge.

*Color.*—Green, (approximately RHS Green Group 137 C) when young, but graduating to a brown color, (approximately RHS Greyed-Orange group N172 A) with advancing senescence. The leaf stipules are generally considered to be early deciduous.

FLOWERS

Flower buds:

*Hardiness.*—No winter injury (bud death) has been noted during the last several years of observation in the central San Joaquin Valley. The new variety of peach tree has not been intentionally subjected to drought or heat stress, and therefore this information is not available.

Date of first bloom: Observed on Mar. 1, 2010.

Blooming time: Considered medium in relative comparison to other commercial peach cultivars grown in the central San Joaquin Valley. The date of full bloom was observed on Mar. 9, 2010. The date of full bloom varies slightly with climatic conditions, and prevailing cultural practices. Flower bud color at pre-bloom and prior to scale separation is green-purple (RHS 187C).

Duration of bloom: Approximately 9 days. This characteristic varies slightly with the prevailing climatic conditions.

Flower type: The variety is considered to have a showy type flower.

Flower size: Considered relatively large. The flower diameter at full bloom, is approximately 49.0 to 54.0 millimeters.

Bloom quantity: Considered abundant.

Flower bud frequency: Normally one to two flower buds appear per node. Only rarely does more than 2 flower buds per node occur.

Petal size: Generally considered medium large for the species.

*Length.*—Approximately 20.0 to 24.0 millimeters.

*Width.*—Approximately 19.0 to 21.0 millimeters.

Petal form: Considered an apically rounded ovate.

Petal count: Nearly always 5.

Petal texture: Glabrous.

Petal color: Considered a light pink at the popcorn stage, (RHS Red-Purple Group 63 D), and darkening with advanced senescence, and the exposure of sunlight to a medium dark pink, (RHS Red-Purple 64 C).

Fragrance: Slight.

Petal claw:

*Form*.—The claw is considered ovate, and is generally medium large when compared to other varieties.

*Length*.—Approximately 10.0-13.0 millimeters.

*Width*.—Approximately 9.0 to 11.0 millimeters.

Petal margins: Generally considered variable, from nearly smooth to moderately undulate.

Petal apex: Occasionally a small, axially centered groove is noted.

Flower pedicel:

*Length*.—Considered medium long with an approximate length of about 4.0 to about 5.0 millimeters.

*Diameter*.—Approximately 2.5 millimeters.

*Color*.—A medium brown, approximately (RHS Grey-Brown Group N199 D).

Floral nectaries:

*Color*.—Considered a dull orange-red (RHS Orange-Red Group N34 B).

*Upper portion of the calyx*.—Surface Texture. — Generally glabrous. Color. — A dull red, (approximately RHS Greyed-Purple Group 183 A).

*Lower portion of the calyx*.—Surface Texture. — The surface has a short, fine pubescent texture. Size. — Average, and ovate in form. Color. — A dull red, (approximately RHS Greyed-Red Group 178 A).

Anthers:

*Generally*.—Average, to above average in length.

*Color*.—Red to reddish-orange when viewed dorsally prior to dehiscence, (approximately RHS Greyed-Red Group 180 A).

Pollen production: Abundant.

*Color*.—Considered yellow in color, (approximately RHS Yellow-Orange Group 17 B).

Fertility: Self-fertile.

Filaments:

*Size*.—Approximately 15.0 to 19.0 millimeters in length.

*Color*.—Considered white to a pinkish-white, (RHS Red Purple Group 62 D).

Pistil:

*Number*.—Usually one, and only rarely more than one.

*Generally*.—Average in size.

*Length*.—Approximately 18.0 to about 20.0 millimeters in length including the ovary.

*Color*.—Considered a very pale green, (approximately RHS Yellow Green Group 151D).

*Surface texture*.—The variety has a long pubescent pistil.

FRUIT

Maturity when described: Firm ripe condition (shipping ripe).

Date of first picking: Jun. 12, 2010.

Date of last picking: Jun. 17, 2010. The date of harvest varies slightly with the prevailing climatic conditions and the current cultural practices.

Size:

*Generally*.—Considered large, and uniform.

Average cheek diameter: Approximately 68.0 to about 75.0 millimeters.

Average axial diameter: Approximately 65.0 to about 72.0 millimeters.

Typical weight: Approximately 258.0 grams. This characteristic is quite dependent upon the prevailing cultural practices, and therefore is not particularly distinctive of the new variety.

Fruit form:

*Generally*.—Considered slightly oblate. The fruit is generally uniform in symmetry.

Fruit suture: No callousing or stitching exists along the suture line.

Suture:

*Color*.—Generally blushed to the same degree as the skin, (approximately RHS Red Group 42 A).

Ventral surface:

*Form*.—Quite even and uniform in appearance when it is viewed from the lateral sutorial plane. The suture shape often exhibits a slight, rounded protrusion in the region of the ventral axis.

Apex:

*Shape*.—Rounded.

Base:

*Shape*.—Generally smooth.

Stem cavity:

*Generally*.—It extends in an oval form which is generally oriented along the sutorial plane. The stem cavity is rounded and uniform in shape. The average depth of the stem cavity is about 7.0 mm. The average width of the stem cavity is about 12.0 mm. The average length of the stem cavity when measured in the sutorial plane is about 22.0 mm.

Fruit skin:

*Thickness*.—Considered medium in thickness, and tenacious to the flesh.

*Surface texture*.—Short, fine and pubescent. The pubescence is moderately abundant.

*Taste*.—Non-astringent.

*Tendency to crack*.—Not observed in the previous years of observation and evaluation.

Fruit skin color:

*Blush color*.—Generally speaking, a red blush exists on a majority of the skin of the fruit (approximately RHS Red Group 42 A), and is typically more present on the portions of the fruit facing the sunlight. The blush covers approximately 80-90% of the fruit skin surface. The percentage of the blush on the fruit skin surface can vary, and is generally dependent upon the fruit's exposure to direct sunlight; specific fruit maturity; and also the prevailing ecological and cultural conditions under which the fruit is grown. It should be noted that the presence of darker pigmentation which causes 'striping' or 'tigering,' is generally observed laterally, and above the equatorial plane and generally increases in frequency in progression toward the fruit's apex. This additional pigmentation generally deepens the hue of the surrounding surface.

*Ground color*.—Yellow, (approximately RHS Yellow Group 10 A). The ground color of the fruit can vary significantly based upon the maturity of the fruit when this measurement is taken.

Fruit stem:

*Size*.—Medium in length, approximately 6.0 to about 10.0 millimeters.

*Diameter*.—Approximately 2.0 to about 3.0 millimeters.

*Color*.—Pale yellow-green, (approximately RHS Yellow-Green Group N144 B).

Fruit flesh:

*Ripening.*—Considered even.

*Texture.*—Firm, juicy and dense. Considered firm yet melting.

*Fibers.*—Few are found.

*Aroma.*—Slight.

*Eating Quality.*—Considered very good.

*Flavor.*—Considered very sweet and with moderate acidity. The flavor is considered both pleasant and balanced.

*Juice production.*—Moderate.

*Brix.*—About 12.0 to 15.0 degrees. This characteristic varies slightly with the number of fruit per tree; the maturity of fruit when harvested; the prevailing cultural practices; and the ambient climatic conditions.

*Flesh color.*—It is considered an orange-yellow, (approximately RHS Yellow Group 10 D.

STONE

Type: Considered clingstone.

Size: Considered medium for the variety. The stone size varies significantly depending upon the tree vigor, the crop load and the prevailing growing and cultural conditions.

Length: Average, about 30.0 to about 35.0 millimeters.

Width: Average, about 26.0 to about 31.0 millimeters.

Diameter: Average, about 20.0 to about 24.0 millimeters.

Form: Roughly ovoid.

Form: Roughly ovoid.

Base: Shape—The stone is considered shortly attenuate.

Apex: Shape—The stone exhibits a slight to prominently acute apex.

Stone surface:

*Surface texture.*—Considered irregularly furrowed toward the apex. Further, more pitting exists in the mid-portion of the stone (laterally), and is more common toward the base.

*Ridges.*—Ridging is generally more prominent, and is usually oriented parallel, and laterally relative at the ventral and dorsal margins.

*Ventral edge.*—The ventral edge is generally considered troughed with two reasonably distinguished edges running parallel to, and on both sides of the stone's suture. These distinct edges continue from the hilum to the apex.

*Dorsal edge.*—Shape — Generally considered moderately rough, and uneven. The folds of the surface ridges appearing on the external margins often end abruptly along the suture.

Stone color: The color of a mature, dry stone is generally considered a pinkish tan, approximately (RHS Orange-Red Group 31 C). This coloration depends, to some degree, on the moisture content of the stone. This color is variable, however, and may also be affected by oxidation and sun bleaching. This variability in the color, depending upon the stone's maturity, and sun exposure, would be considered an inconsistent descriptor of this new variety.

Tendency to split: Splitting has rarely been noted.

Kernel:

*Size.*—The kernel is considered medium-small in size.

*Form.*—Considered generally ovoid.

*Pellicle.*—Slightly pubescent.

*Color.*—(RHS Greyed-Orange Group 163 C).

Use: The present variety 'Burpeachtwentyseven' is considered to be a peach tree of the early season of maturity, and which produces fruit which are considered to be firm, attractively colored, and which are useful for both local and long distance shipping.

Keeping quality: Appears excellent. The fruit of the present variety has stored well for periods of up to 30 days after harvest at 1.0 degree Celsius.

Shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by Plant Letters Patent is:

1. A new distinct variety of peach tree, substantially as illustrated and described, and which is characterized principally as to novelty by producing an attractively colored yellow-fleshed, clingstone peach which is mature for harvesting and shipment approximately June 12 to June 19 under the ecological conditions prevailing in the San Joaquin Valley of central California.

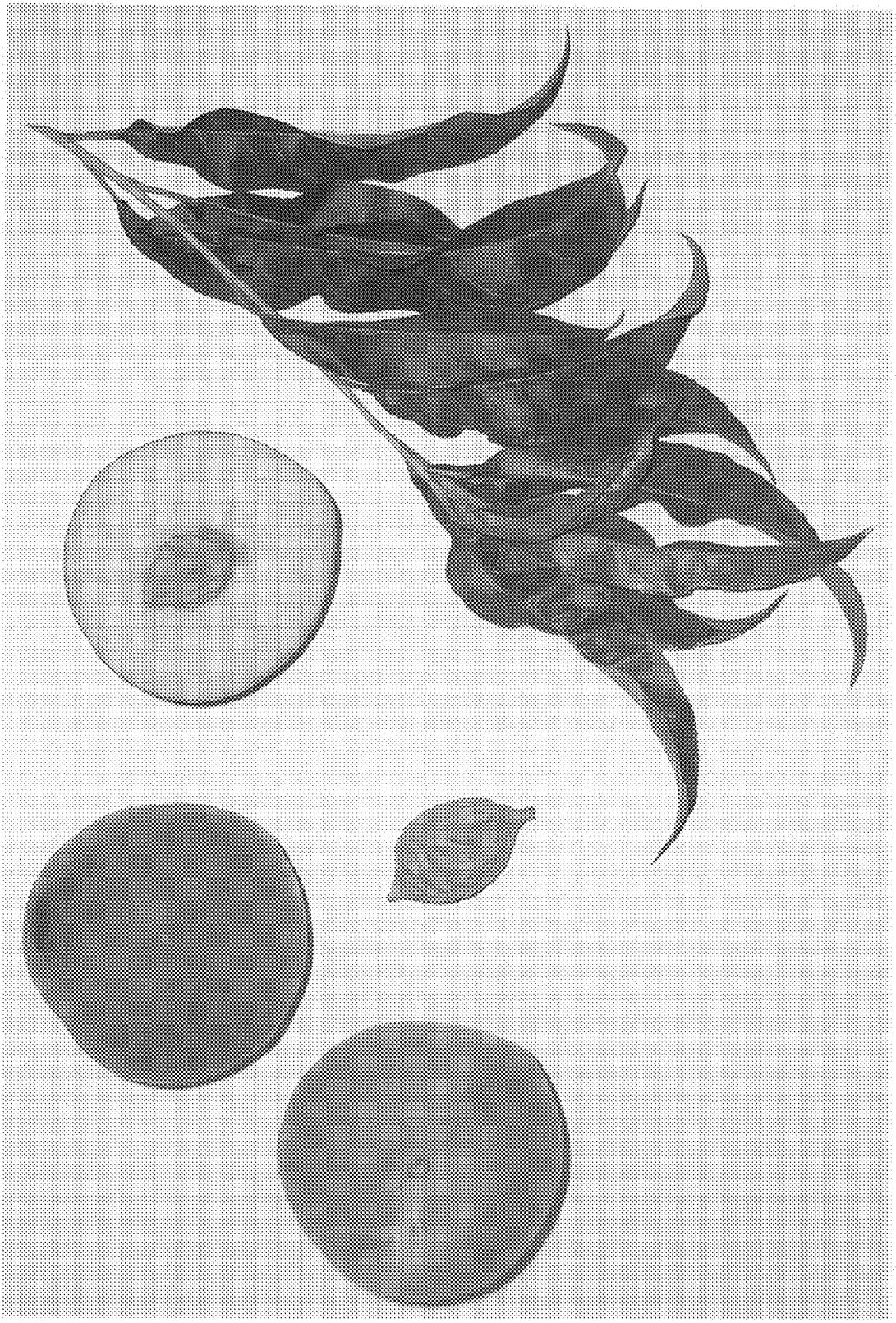

* * * * *